(12) United States Patent
Goetzinger et al.

(10) Patent No.: US 7,860,579 B2
(45) Date of Patent: Dec. 28, 2010

(54) DELIVERY SYSTEM, METHOD, AND ANCHOR FOR MEDICAL IMPLANT PLACEMENT

(75) Inventors: David Joseph Goetzinger, Livonia, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 894 days.

(21) Appl. No.: 11/684,910

(22) Filed: Mar. 12, 2007

(65) Prior Publication Data

US 2007/0179583 A1 Aug. 2, 2007

Related U.S. Application Data

(63) Continuation-in-part of application No. 10/898,053, filed on Jul. 24, 2004, now Pat. No. 7,317,951.

(60) Provisional application No. 60/780,604, filed on Mar. 10, 2006, provisional application No. 60/489,974, filed on Jul. 25, 2003, provisional application No. 60/491,002, filed on Jul. 30, 2003.

(51) Int. Cl.
*A61N 1/00* (2006.01)

(52) U.S. Cl. .................................... 607/126

(58) Field of Classification Search ................. 128/885, 128/898; 600/561, 486; 607/126, 51, 123, 607/125, 116, 2, 122; 604/174
See application file for complete search history.

(56) References Cited

U.S. PATENT DOCUMENTS

| | | | |
|---|---|---|---|
| 6,442,435 B2 * | 8/2002 | King et al. | 607/117 |
| 2003/0078465 A1 * | 4/2003 | Pai et al. | 600/16 |
| 2003/0093104 A1 * | 5/2003 | Bonner et al. | 606/185 |

* cited by examiner

*Primary Examiner*—George Manuel
*Assistant Examiner*—Robert N Wieland
(74) *Attorney, Agent, or Firm*—Hartman & Hartman, P.C.; Gary M. Hartman; Domenica N.S. Hartman

(57) ABSTRACT

An anchor for a medical implant, a method of manufacturing an anchor, and a delivery system and method for delivering a medical implant, such as for monitoring physiological parameters, for example, for diagnosing and/or monitoring and/or treating cardiovascular diseases, such as CHF and CHD. The anchor includes a base member, arms, legs, features for securing the medical implant to the base member, and features for connecting the anchor to a connector. The anchor has a deployed configuration in which the arms radially project from a first end of the base member and the legs radially project from an opposite end of the base member. When deployed, the arms and legs terminate at extremities that are opposing but not aligned with each other.

56 Claims, 9 Drawing Sheets

US 7,860,579 B2

DELIVERY SYSTEM, METHOD, AND ANCHOR FOR MEDICAL IMPLANT PLACEMENT

CROSS REFERENCE TO RELATED APPLICATIONS

This application claims the benefit of U.S. Provisional Application No. 60/780,604, filed Mar. 10, 2006, and is a continuation-in-part patent application of U.S. patent application Ser. No. 10/898,053, filed Jul. 24, 2004, now U.S. Pat. No. 7,317,951 which claims the benefit of U.S. Provisional Application Nos. 60/489,974, filed Jul. 25, 2003, and 60/491,002, filed Jul. 30, 2003. The contents of these prior applications are incorporated herein by reference.

BACKGROUND OF THE INVENTION

The present invention generally relates to implantable medical devices and implant procedures, including devices and procedures used to monitor physiological parameters of the living (e.g., human) body. More particularly, the invention relates to anchors for a medical implant, methods of manufacturing anchors, and methods of placing medical implants, wherein the anchors and methods are suitable for use in procedures performed to diagnose, monitor, and/or treat cardiovascular diseases, including congestive heart failure (CHF) and congenital heart disease (CHD), for example, by monitoring pressures in the left side of the heart.

CHF is a condition in which the heart fails to pump efficiently, and currently affects about 4.7 million patients (over 400,000 new patients per year in the U.S.). Estimates are that CHF accounts for about 5 to 10% of all hospitalizations and costs over $38 billion in the U.S. Following diagnosis of CHF, physicians typically monitor disease progression on a continuing basis to better tailor treatment. The best course of action for a tailored treatment involves monitoring pressures of the left side of the heart, particularly left ventricular end diastolic pressure (LVEDP, also known as left ventricular filling pressure) and mean left atrium pressure (MLA). These pressures are recognized as the best parameters for characterizing CHF in patients. Clinical evaluation of LVEDP or MLA is currently limited to cardiac catheterization procedures, which provide a snapshot of pressure data a few times per year at most, carries morbidity, and is expensive.

CHD includes various defects of the heart that are typically present at birth. A particularly complex example is a heart that has only one functional ventricle. In order to provide patients with appropriate solutions, multiple surgical procedures are required. These procedures enable the single ventricle to serve as the systemic ventricle, while the lungs receive blood flow via different anastomosis (for example, a Fontan baffle). A key dilemma in the treatment of these patients is the timing of the different surgical stages. The inclination is to perform the surgeries at a younger age. However, if performed too early, the outcome can be dismal. The hemodynamic status and timing of the different surgical stages can be assessed by invasive cardiac catheterization to measure pulmonary artery pressure and resistance. However, as noted above with respect to monitoring CHF patients, cardiac catheterization provides only a single measurement in time and has been associated with morbidity and mortality in CHD patients.

Using an implant to monitor pressures of the left side of the heart is very challenging for many reasons, most importantly the potentially fatal outcome of any thrombi caused by the implant. Miniaturized sensors capable of being chronically implanted are gaining particular attention, especially those made produced by MEMS (microelectromechanical systems) technologies. Notable examples include devices disclosed in commonly-assigned U.S. Pat. Nos. 6,926,670 and 6,968,743, and commonly-assigned U.S. patent application Ser. Nos. 10/679,888, 10/679,916, 10/679,926, 10/677,674, and 10/677,694, which collectively have achieved significant advances for the use of implants in diagnosing, monitoring, and/or treating cardiovascular diseases. When adapted to monitor pressure, the devices disclosed in these patent documents generally have two primary components: the implant comprising an implantable telemetric pressure sensor that is batteryless or makes use of a small battery, and a companion hand-held reader. The implant further preferably includes custom electronics for processing the output of the sensor and an antenna for telemetry and, if necessary or desired, for tele-powering the sensor. Telemetry and tele-powering can be achieved via various techniques, including but not limited to magnetic telemetry (including RF), acoustic waves, ultrasonic waves, with the currently preferred technique typically being magnetic telemetry. The reader transmits power to the sensor, and the sensed pressure is in turn transmitted back to the reader. Data collected from the sensor can then be used by a physician to tailor the treatment of the patient. In some cases, the implant may also be configured or adapted to perform additional functions, such as delivering a drug or an electric signal to the muscles/nerves.

In view of the foregoing, it can be appreciated that miniaturized implants of the types described above can provide chronic, continuous bio-pressure measurements and support the trend toward home health monitoring. Advancements have also been achieved in regard to the delivery and anchoring of such medical implants within the heart for monitoring heart pressures. Notable examples include delivery and anchoring systems disclosed in commonly-assigned U.S. patent application Ser. No. 10/730,439 and U.S. Patent Application Publication No. 2005/0065589. Nonetheless, further improvements are desired, particularly in regard to the reliability and manufacturability of anchoring systems and the simplicity of their delivery.

BRIEF SUMMARY OF THE INVENTION

The present invention provides an anchor for a medical implant, a method of manufacturing an anchor, and a delivery system and method for delivering a medical implant, such as for monitoring physiological parameters. The invention is particularly directed to implantation of physiologic sensors/actuators for diagnosing and/or monitoring and/or treating cardiovascular diseases, such as CHF and CHD.

The anchor of this invention includes a base member, a plurality of arms, a plurality of legs, a feature for securing the medical implant to the base member, and a feature for connecting the anchor to a connector. The base member has an axis and first and second ends in oppositely-disposed first and second directions, respectively, along the axis of the base member. The anchor has a deployed configuration in which the arms radially project from the first end of the base member, and the legs radially project from the second end of the base member. Each arm has a first portion extending in the first direction from the first end of the base member and a second portion extending in the second direction from the first portion thereof. Each leg has a first portion extending in the second direction from the second end of the base member and a second portion extending in the first direction from the first portion thereof. When deployed, the arms and legs terminate at extremities that are opposing but not aligned with each other.

A preferred method of manufacturing the anchor of this invention generally entails cutting a unitary body to form the base member, the arms, the legs, and the connecting means, and then deforming the arms, the legs, and the connecting means.

The delivery system of this invention includes a catheter assembly containing a catheter, an anchor, and a feature for connecting the anchor to the catheter. The anchor includes a base member with first and second ends in oppositely-disposed first and second directions, arms and legs extending from the base member, and a feature for securing the medical implant to the base member. The connecting feature includes a joint that enables articulating movement of the anchor relative to the catheter in directions transverse to an axis of the catheter.

The delivery method of this invention involves coupling an anchor to an end of a catheter and securing the medical implant to the anchor, passing the catheter with the anchor coupled thereto through a sheath, placing an end of the sheath through an internal wall of a human body so that the anchor is positioned within that portion of the sheath within the internal wall, retracting the sheath so as to release a plurality of arms from the anchor that engage a distal surface of the internal wall, and then further retracting the sheath so as to release a plurality of legs from the anchor that engage a proximal surface of the internal wall.

In view of the above, it can be seen that the present invention provides an uncomplicated anchor and procedure of placing a variety of implantable medical devices, including those adapted to monitor physiological parameters including pressures within the heart. The configuration of the anchor addresses delivery issues, including delivery method, delivery equipment, implant design, and anchor location, that arise when employing chronically implanted physiologic devices, sensors, and actuators to diagnose and/or monitor and/or treat cardiovascular diseases such as CHF and CHD. Notably, the anchor and its delivery find application in the very challenging application of monitoring the pressure of the left side of the heart. Medical implants that can be placed and anchored in accordance with this invention can operate wirelessly or can be connected to other devices (such as pacemakers) using electrical wires (e.g., pacemaker leads, polymer based flex cables, or wires) or other types of communications means (e.g., ultrasonic, optical, or electrophysiology signals).

Other objects and advantages of this invention will be better appreciated from the following detailed description.

DETAILED DESCRIPTION OF THE INVENTION

Figure 1:
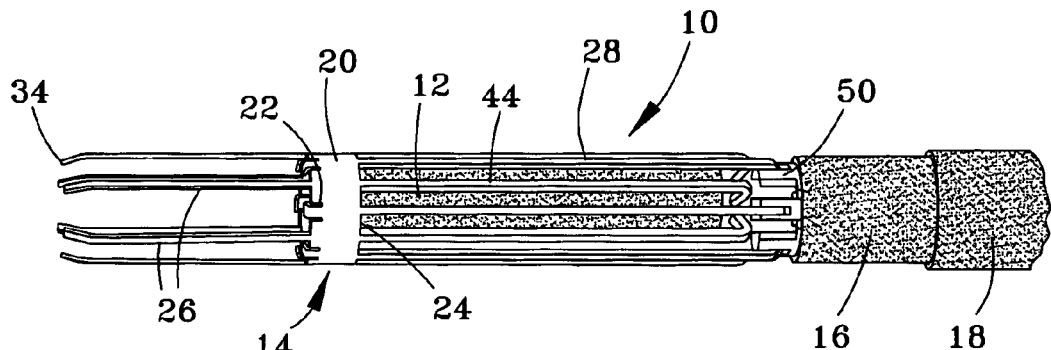
FIG. 1 is a perspective view of an implant delivery system in accordance with a first embodiment of this invention.
Figure 12:
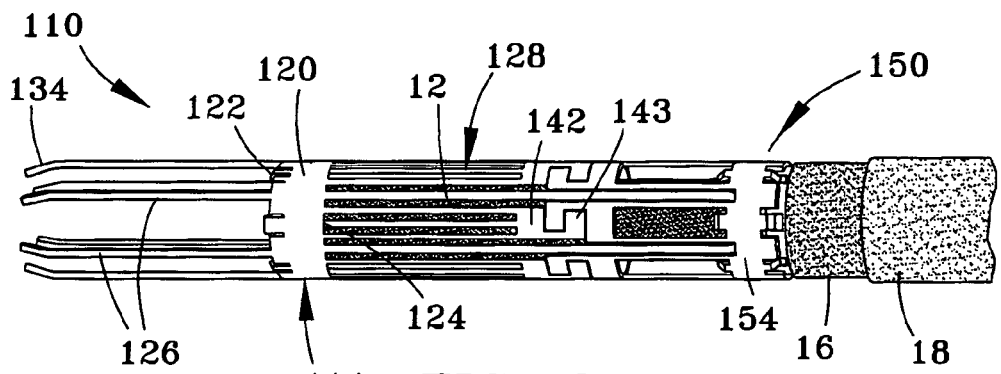
FIG. 12 is a perspective view of an implant delivery system in accordance with a second embodiment of this invention.

FIGS. 1 and 12 depict delivery systems 10 and 100 suitable for delivering and securing a medical implant 12 to a wall, such as a wall of a cardiovascular organ, in accordance with embodiments of the present invention. As a notable example, the wall can be an atrial septum and the implant 12 measures physiological parameters of the heart, such as LVEDP or MLA pressure. The implant 12 may be any one of a variety of types of implants currently known or developed in the future, and the scope of the present invention is not limited in any way by the type and operation of the implant 12. Implantable devices capable of being delivered with the present invention include but are not limited to devices disclosed in commonly-assigned U.S. Pat. Nos. 6,926,670 and 6,968,743, and commonly-assigned U.S. patent application Ser. Nos. 10/679,888, 10/679,916, 10/679,926, 10/677,674, and 10/677,694.

With reference first to the embodiment of FIGS. 1 through 11, the implant delivery system 10 is represented as including an anchor 14 in which an implant 12 is secured, a positioning catheter 16 to which the anchor 14 is coupled, and a sheath 18 in which the catheter 16 and its attached anchor 14 are telescopically received. As such, the anchor 14, catheter 16, and sheath 18 are all generally coaxial. In the preferred embodiment, the positioning catheter 16 is hollow to enable fluids to be delivered to or removed from the deployment site of the anchor 14. The sheath 18 can be of any suitable type known in the art or subsequently developed.

Figure 5:
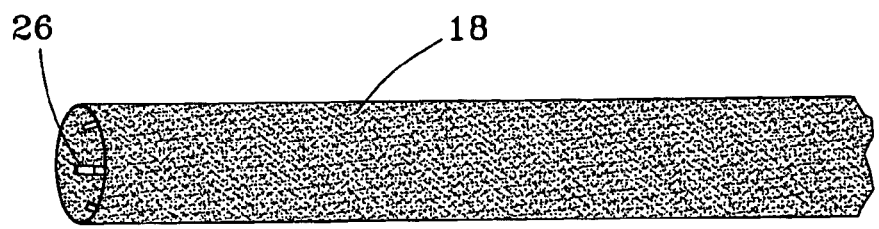
FIG. 5 is a perspective view of the implant delivery system of FIG. 1, showing the anchor and its implant retracted into a sheath in preparation for delivering the implant.

The anchor 14 is depicted in FIG. 1 in what will be termed a stowed configuration, meaning the configuration of the anchor 14 while within the sheath 18 (FIG. 5). The stowed configuration is also depicted in the isolated view of the anchor 14 in FIG. 2. In contrast, FIG. 3 depicts the anchor 14 in a deployed configuration, meaning the configuration of the anchor 14 when extended outside the sheath 18 so that appendages of the anchor 14 are allowed to deploy, as described below. As such, though FIG. 1 shows the anchor 14 in its stowed configuration for illustrative purposes, the position of the anchor 14 outside the sheath 18 would ordinarily result in the deployed configuration shown in FIG. 3.

Figure 2:
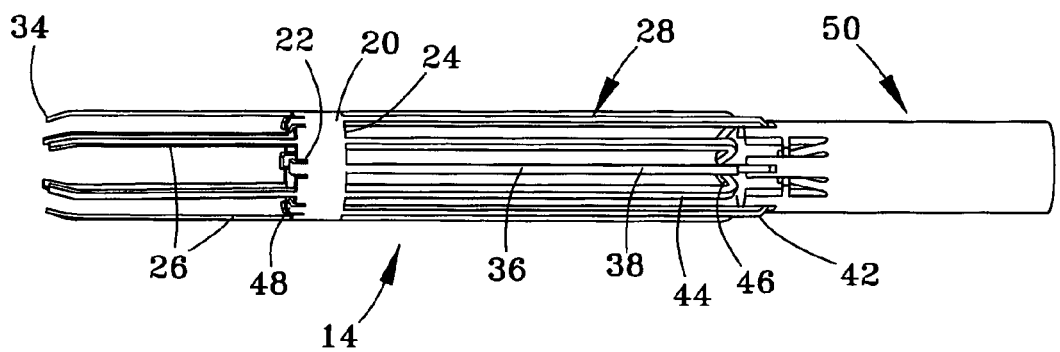
FIGS. 2 and 3 are isolated perspective views of an anchor of the implant delivery system of FIG. 1, showing the anchor in both stowed and deployed configurations, respectively.
Figure 3:
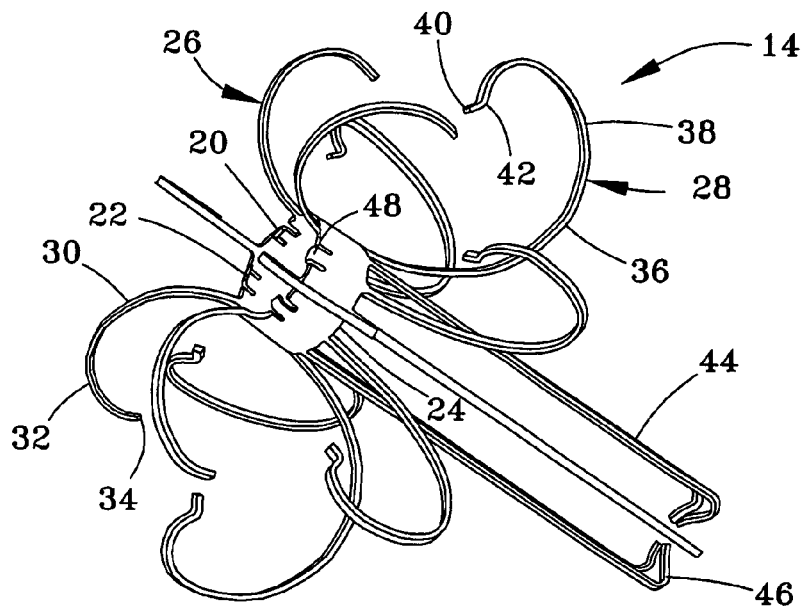

In FIGS. 1 through 3, the anchor 14 is shown as having an annular-shaped base 20 surrounding the implant 12. The base 20 has oppositely-disposed first and second ends 22 and 24 corresponding to oppositely-disposed first and second directions along the axis of the base 20. For convenience, these directions will be referred to as distal and proximal directions, and various structures of the system 10 including the ends 22 and 24 of the base 20 will be described as being distal or proximal, to reflect the orientation of the anchor 14 during an implantation procedure described below, though it should be understood that the invention is not necessarily limited to such an orientation. When stowed (FIGS. 1 and 2), arms 26 and legs 28 extend substantially parallel to the axis of the base 20 from its distal and proximal ends 22 and 24, respectively. When deployed (FIG. 3), the arms 26 and legs 28 acquire arcuate shapes that preferably lie entirely within angularly spaced radial planes, each containing the axis of the base 20. The deployed arms 26 generally deploy in the proximal direction to project substantially radially from the base 20, with a first portion 30 of each arm 26 generally extending in the distal direction from the distal end 22 of the base 20, and a second portion 32 of each arm 26 generally extending in the proximal direction from the first portion 30. Each second portion 32 terminates with an extremity or tip 34, which is generally parallel to the axis of the base 20, radially offset from the axis. Similarly, each deployed leg 28 projects substantially radially from the base 20. However, the legs 28 generally deploy in the distal direction (opposite that of the arms 26), with a first portion 36 of each leg 28 generally extending in the proximal direction from the proximal end 24 of the base 20, a second portion 38 of each leg 28 generally extending in the distal direction from its corresponding first portion 36, and each second portion 38 terminating with an extremity or tip 40 that is generally parallel to but radially offset from the axis of the base 20. In addition to their direction of deflection, the legs 28 differ from the arms 26 by having a third portion 42 between its second portion 38 and tip 40, and generally oriented radially relative to the axis of the base 20, necessitating an additional curve to each leg 28 to orient the tip 40 substantially parallel to the axis of the base 20.

Figure 11:
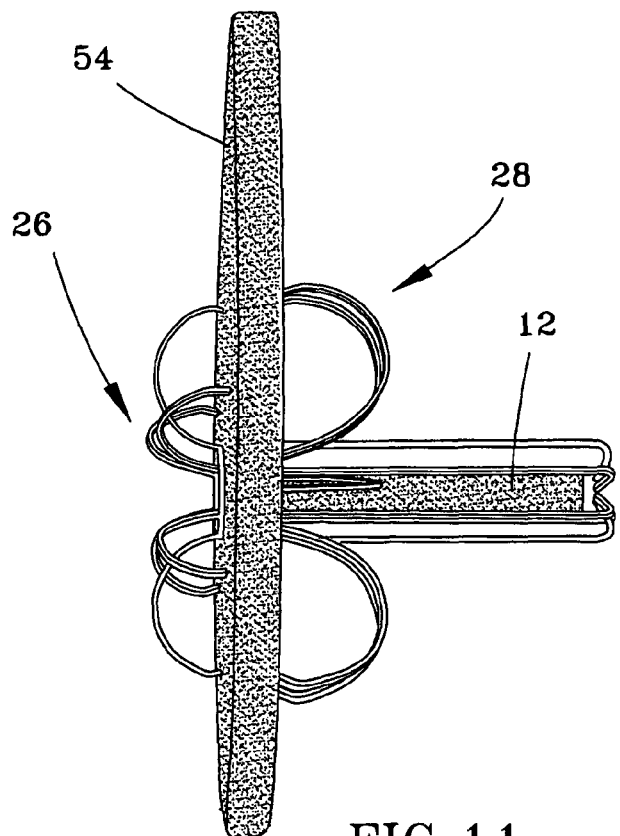

As evident from FIGS. 1 through 3, each arm 26 and leg 28 lies in a different radial plane, with the result that the arms 26 and legs 28 are not collinear when stowed and their tips 34 and 40 do not directly oppose each other when deployed, such that a wall into which the anchor 14 is inserted would not be locally compressed by directly opposing arms 26 and legs 28, as will become evident from FIG. 11. Furthermore, the tips 34 and 40 of the arms 26 and legs 28 are capable of piercing a wall in which the anchor 14 is placed, so that the tips 34 and 40 can become embedded in the wall without puncturing the wall. In this manner, the arms 26 and legs 28 cooperate to secure the anchor 14 to a wall (as represented in FIG. 11), so that the anchor 14 is able to resist axial and rotating forces that might dislodge the anchor 14 and its implant 12. Furthermore, the minimized compressive forces applied by the anchor 14 to the septum of a heart is believed to reduce tissue killed after implantation. The configurations of the arms 26 and legs 28 and their opposing actions also accommodate walls of differing thicknesses.

FIGS. 1 through 3 further show the anchor 14 as having retention legs 44 that extend from the proximal end 24 of the base 20 in the proximal direction and parallel to the axis of the base 20. Each retention leg 44 terminates with a finger 46 that extends radially inward toward the axis of the base 20. At the distal end 22 of the base 20, fingers 48 extend radially inward from the circumference of the base 20. As evident from FIG. 1, together the base 20, retention legs 44, and fingers 46 and 48 define a cage for the implant 12, with opposite ends of the implant 12 abutting the fingers 46 and 48. The implant 12 can be placed within the cage through openings defined by the base 20 or retention legs 44, and then retained by crimping the appropriate fingers 46 or 48 over the opening. Preferably, the implant 12 is inserted through the base 20 and retained by crimping the base fingers 28, and the length of the retention legs 44 are sized so that their fingers 46 provide a spring load to positively retain the implant 12 within the cage, so that pulsation effects of the heart or blood flow do not cause movement of the implant 12 that might lead to potentially false signal data. While a cylindrical implant 12 is shown in FIG. 1, the functionality of the anchor 14 is not dependent on any particular type of implant, and can be readily adapted to secure a variety of different types of implants with different sensing technologies. Furthermore, though fingers 46 and 48 are preferred for retaining the implant 12, it should be appreciated that retention of the implant 12 in the anchor 14 can be accomplished in different ways, including without limitation one, more, or any combination of the following methods: cam slot, threading, snapping, snap latch, latch fingers, spring latch, latch fingers with a catheter sheet on top to release the latch, use of one or more guidewires or catheters in order to either latch or release coupling means (such as latching fingers), dissolvable glues, temporary glues, thermal glues, heated shape memory latches, unheated shape memory latches, heated mechanical means, piezoelectric release system, hydraulic coupling systems, pneumatic coupling systems, magnetic coupling systems, etc.

Figure 4:
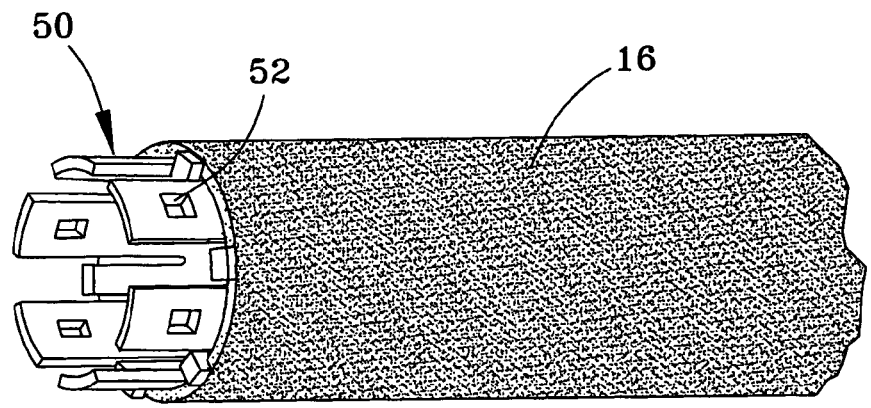
FIG. 4 is an isolated perspective view of a positioning catheter of the implant delivery system of FIG. 1.

As further evident from FIGS. 1 and 2, the tips 40 of the legs 28 are configured to couple with a connector 50 when in their stowed position. The connector 50 has a tubular shape sized to be received and secured in the end of the positioning catheter 16. As shown in FIG. 4, the connector 50 is formed to have slots or windows 52 corresponding in number to the legs 28 and sized to receive the tips 40 of the legs 28. By using the sheath 18 to hold the tips 40 of the legs 28 in their respective windows 52, as is the case when the positioning catheter 16 and anchor 14 are disposed within the sheath 18 (FIG. 5), the anchor 14 is secured to the catheter 50 through its connector 50, but can be quickly released by retracting the sheath 18 to expose the legs 28 and thereby release the leg tips 40 from their windows 52. Another desirable feature of the leg-connector coupling scheme described above is that the tips 40 and windows 52 do not form a rigid joint, but instead create an articulating joint in that the anchor 14 has some freedom of movement in directions transverse to the axis of the catheter 16. This aspect of the invention facilitates threading the catheter assembly (catheter 16 and anchor 14) through a patient's arterial system.

According to a preferred aspect of the invention, the entire anchor 14 can be fabricated as a unitary body, and therefore without resorting to any assembly techniques involving metallurgical joining (e.g., welding, brazing, etc), mechanical joining (e.g., fasteners, threads, latches, deformation, etc.), or bonding (e.g., adhesive), though such assembly methods are within the scope of the invention. As such, the entire anchor 14 can be fabricated from a single preform, such as by cutting the preform to form the base 20, arms 26, and legs 28 and 44, and then deforming the base 20, arms 26, and legs 28 and 44 as required to form the anchor 14 shown in FIGS. 1 through 3.

Many existing medical implantable devices for use in the heart utilize NITINOL®, a "shape memory" nickel-titanium alloy that enables an umbrella-like structure folded inside a catheter for delivery to later automatically expand once outside the catheter for implantation. In a preferred embodiment, the anchor 14 is formed of NITINOL or another suitable shape memory material. According to another preferred aspect, the anchor 14 can be manufactured primarily by laser cutting techniques performed on solid tubes of a shape memory material, rather than primarily using welding techniques as typically done in the prior art. Fabrication of the anchor 14 using laser cutting techniques provides at least two advantages. First, the reliability of the anchor 14 is much higher since its components (base 20, arms 26, and legs 28 and 44) are integral portions of a single metal piece. Welded joints possess higher risk of failure than that possible with the preferred unitary construction for the anchor 14. Secondly, the cost of manufacturing can be significantly lower than would be possible if relying primarily on welding to form the anchor 14.

In practice, a NITINOL tube can be cut by laser alone to form an anchor preform. The laser cutting operation can be performed as an automated process based on drawing files using commercial mechanical design software. The tubular-shaped anchor preform is then formed into the desired 3-D structure (i.e., the deployed configuration of FIG. 3) with shape memory by being placed in a mechanical jig and heated to an appropriate temperature to store the shape into the memory of the NITINOL material. After its fabrication, the anchor 14 preferably undergoes chemical passivation in order to reduce the corrosion tendencies of NITINOL in body fluids, and then coated with a suitable biocompatible coating such as parylene.

A key parameter of any wireless, implantable system is the communication distance (both tele-powering and telecommunication) between the implant 12 and a remote readout handheld unit. Since the anchor 14 may be formed of a metal such as NITINOL, there exists a potential that such a metallic anchor could adversely affect (reduce) the communication distance between the implant 12 and the handheld unit (not shown) by acting similar to a Faraday cage. Tests performed using metal implants indicated that telemetry communication distances can be reduced by about two-thirds, such that placing an implant using RF/electromagnetic telemetry inside a metal anchor would not be expected to achieve reasonable performance. To overcome this problem, the anchor 14 is configured to avoid the primary causes of reduced communication distances. Attenuation was determined to depend on parameters including the number of metal loops, the orientation of the loops, and whether the loops are arranged in such a manner as to form a mesh or cage. Fewer numbers of metal loops were associated with longer communication distances. Furthermore, metal loops that are arranged in parallel to the implant communication coil (with or without a ferrite core) were found to not adversely affect the communication distance, while metal wires oriented perpendicular to the implant communication coil (with or without a ferrite core) were found to greatly reduce such magnetic fields. The anchor 14 of the present invention comprises a single loop (the base 20) which does not form a mesh and is limited to one end of the implant 12. In the embodiment shown in FIGS. 1 through 3, the anchor 14 makes satisfactory use of only six arms 26 and six legs 28, none of which lie within the same radial plane. Furthermore, from FIG. 1 it can be appreciated that the size of the cage enclosing the implant 12 and each element (base 20, retention legs 44, and fingers 46 and 48) forming the cage is minimized and their locations selected (including the base 20 limited to one end of the implant 12) so that signals (e.g., data transmission and/or powering) received and transmitted by the implant 12 suffer minimal attenuation. As such, the configuration of the anchor 14 minimizes metal shielding effects, which is beneficial if the implant 12 is wirelessly operated, such as by radio frequency (RF) telemetry, and renders the anchor 14 of this invention practical for use with small implants across long communication distances. The low-profile configuration of the anchor 14 also minimizes the diameter required of the sheath 18 used to delivery the anchor 14 and implant 12, and advantageously results in the anchor 14 exerting minimal stress on the implant 12.

The anchor 14 may be employed to locate the implant 12 in various places, depending on the physiological parameter of interest. For the tailored treatment of chronic heart failure, LVEDP and/or MLA pressure are of most importance, and therefore the left chambers of the heart or immediately attaching vessels are among preferred locations for the implant 12. Because the number of implants is not practically limited by the technology, multiple locations for blood pressure measurement are easily established, including all chambers of the heart, major arteries and appendages. The preferred waveforms to monitor for CHF applications are the pressures of the left atrium. The monitored waveforms may include but not limited to complete detailed LA waveform, particularly accurate MLA pressure, real time, and continuous. It should be mentioned that some aspects of the anchor 14 described above will allow pressure measurements of the right atrium (by locating the pressure sensor at the end of the implant 12 facing the right atrium) or both right and left atriums (for example, using two pressure sensors, one at each end of the implant 12), or direct differential pressure measurement between the right and left atrium (again, for example, using two pressure sensors, one at each end of the implant 12). In addition to or instead of pressure, other parameters can easily be monitored using an implant delivered and placed with the anchor 14. Such parameters include but are not limited to blood chemistry, oxygen level, etc. For example, a hydrogel film (with selectivity to different elements) can be placed on top of a pressure sensor to measure the presence of elements that cause the hydrogel to expand, thereby applying pressure to the pressure sensor.

Thrombogenicity is the primary concern when considering a device for implantation in the left side of the heart, due to the possibility of thrombi reaching the brain. In order to assure such high-level of nonthrombogenicity, the present invention is able to reduce such risks through proper anchor shape, anchor location, and delivery method. Thrombogenesis can be caused by direct chemical interaction with an implant or anchor, and by blood flow turbulence resulting from implant geometry. Regarding the former, the above-noted materials for the anchor 14 are selected to be either biocompatible or covered by biocompatible materials. As to the latter, the present invention provides an anchor configuration and placement capability that greatly reduces protrusion of the implant 12 and anchor 14 into the blood flow path of the left atrium to a minimum level, and also provides a hydrodynamic sensor profile that is minimally disruptive to surrounding blood flow. The implant 12 can be preferably placed with the anchor 14 of this invention at two desirable locations: the atrial septum and left atrial appendage. The atrial septum is believed to be preferable for locating the anchored implant 12. It should be emphasized that, while the implant may be long length (e.g., lengths greater than ten millimeters), the anchor 14 is configured so that only a small portion (e.g., less than two millimeters) of the implant 12 is exposed to the left side of the heart; the rest of the implant 12 is in the septum wall and the right atrium. The pressure sensor is placed at or near the end side of the implant 12 that is exposed to the left side. A preferred location for the pressure sensor is believed to be on the front flat side of the cylindrical implant 12 shown in the Figures, so that only a small portion of the implant 12 will be above the surface of the left side of the heart. Subsequent cell growth over the top of the small exposed area of the implant 12 will further reduce the risk of thrombogenicity.

If placed in the atrial appendage, the implant 12 may be anchored by expanding the anchor 14 and then occluding the appendage. In this case, thrombi formation on the distal end (opposite from sensor) of the occlusion device would not pose a risk to the patient, as evidenced by previous left atrial appendage devices that have been introduced for this very purpose.

A reason for preferring placement in the atrial septum is that there exists FDA-approved, commercially-available medical devices for chronic implantation in this location. These devices, for example, are used to occlude atrial septum defects and other vascular holes. The implant 12 can be anchored to the atrial septum with similar techniques as FDA-approved, commercially-available devices such as the AMPLATZER® family of devices commercially available from AGA Medical, or the CardioSEAL commercially available from NMT Medical. These devices have been shown to be suitable for cardiovascular implantation. As a result, one may take advantage of this existing infrastructure, including standard practices of delivering cardiovascular implants. Another advantage of placing the implant 12 within the wall of the atrial septum is that the potential adverse confounding effects of the muscle contraction on the sampled pressure measurements will be considerably reduced.

Delivery of the implant 12 with the anchor 14 demands such considerations as safety, minimal invasiveness, suitability as an outpatient procedure, ease of operation, preferable use of existing practices, minimum training for the physician/technician, and the ability to allow multiple tries before deploying and releasing the anchor 14. As evidenced by FIG. 1, the preferred delivery method for the anchor 14 is believed to be by catheter delivery, discussed below in more detail with reference to FIGS. 6 through 11. To minimize catheter diameter, the implant 12 is preferably small and thin. Delivery and placement of the anchor 14 is able to make use of standard current practices in the cardiovascular field to reduce both time and cost of R&D and manufacturing, create comfort and confidence in cardiologists, and make FDA process easier. The anchor 14 is configured so that, after it is coupled to the connector 50 of the positioning catheter 16 are placed in the sheath 18, the diameter of the stowed anchor 14 is equal or as close as possible to the diameter of the original tube from which the preform was laser cut. This approach renders the smallest possible diameter of the catheter 16 and sheath 18.

Figure 6:
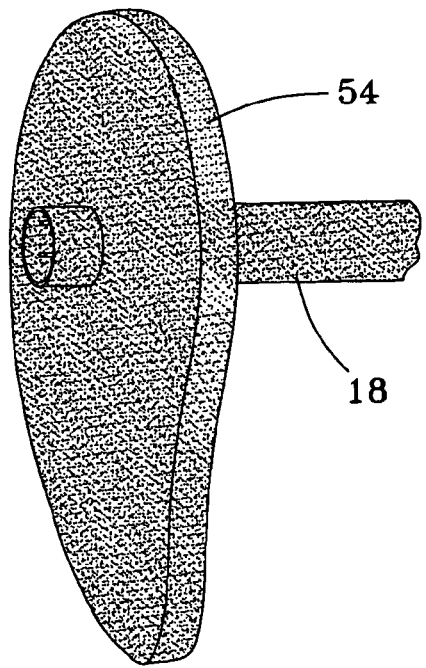
FIGS. 6 through 11 are perspective views representing procedural steps when placing the anchor and implant of FIG. 1.
Figure 7:
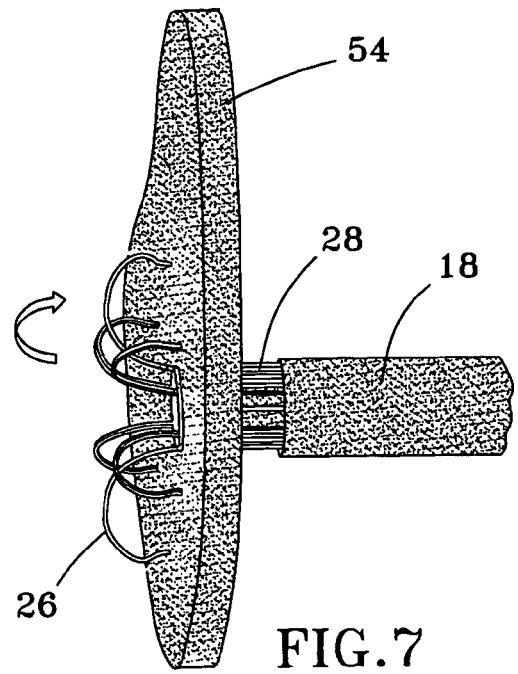
Figure 8:
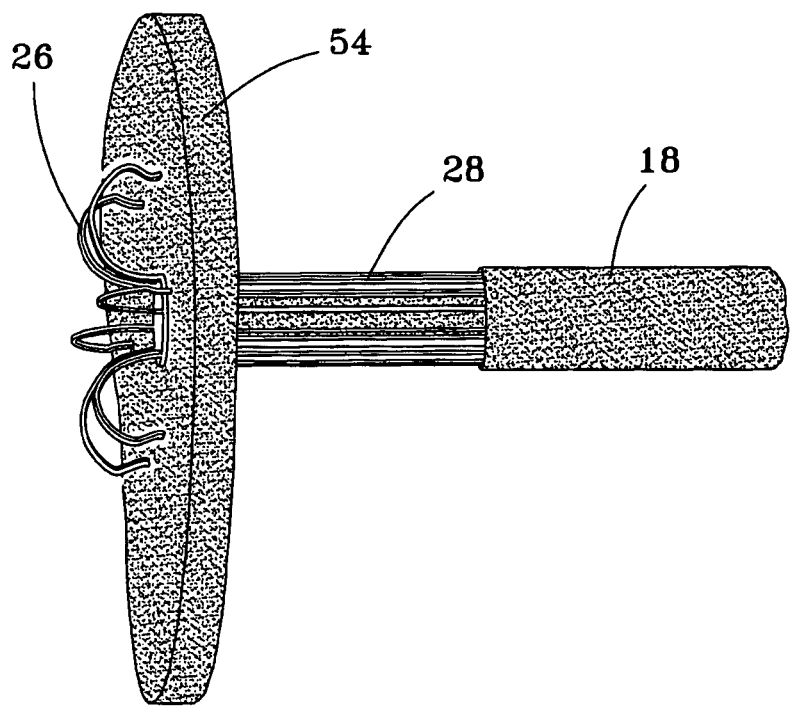
Figure 9:
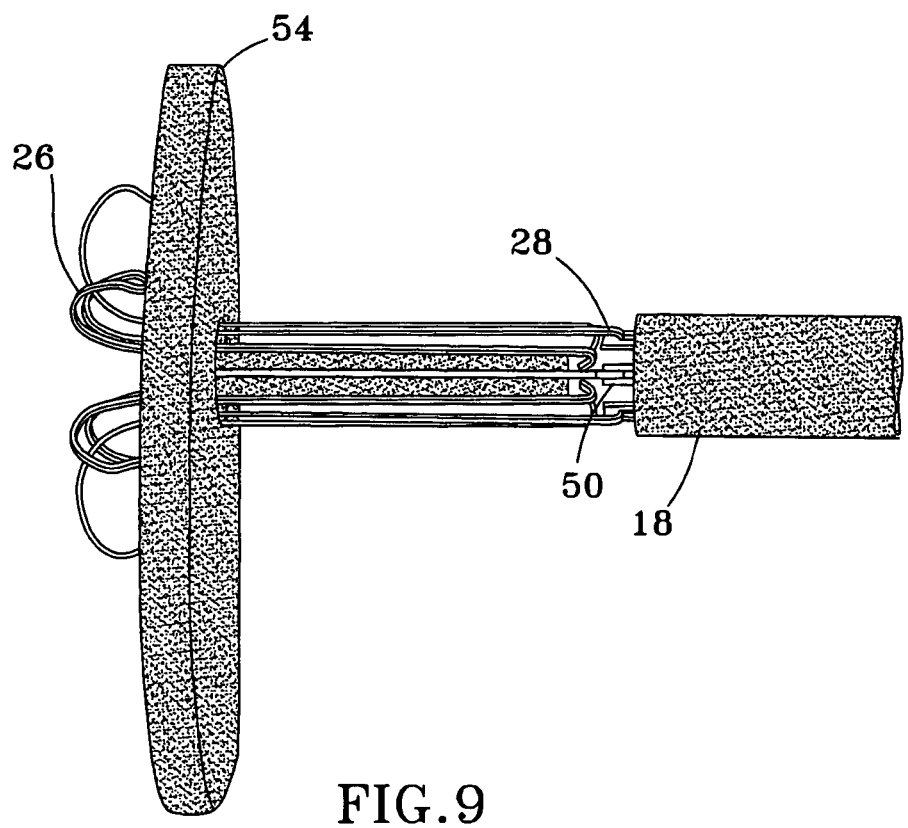
Figure 10:
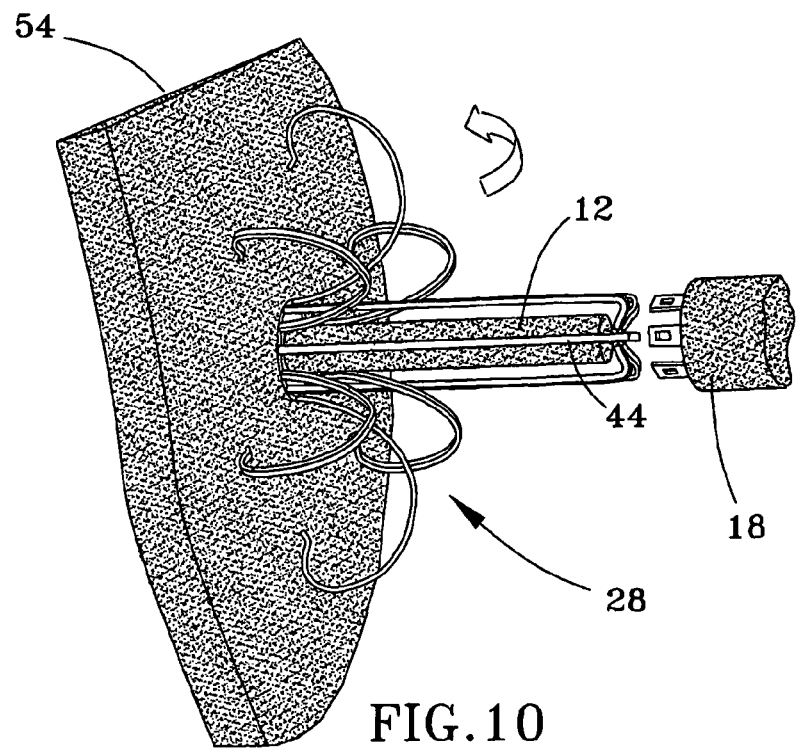

FIGS. 6 through 11 represent a series of steps depicting the procedure for delivering and implanting the anchor 14 and its implant 12 in a wall, such as the atrial septum 54. Using a standard cardiology guidewire via a standard procedure (not shown), the sheath 18 is passed through a patient's arterial system and placed through the atrial septum 54, after which the catheter 16 with its anchor 14 and implant 12 are passed through the sheath 18 until located within the distal end of the sheath 18 as shown in FIG. 6. FIG. 7 depicts the result of slight retraction of the sheath 18 to the extent that the arms 26 of the anchor 14 are released from the sheath 18 and the shape-memory property of the anchor material causes the arms 26 to deploy in the proximal direction so that the tips 34 of the arms 26 engage and become embedded in the distal surface of the septum 54. The sheath 18 is then further retracted as sequentially depicted in FIGS. 8 and 9, with the latter showing the sheath 18 sufficiently retracted to expose the entire lengths of the legs 28. As with FIG. 1, though FIG. 9 shows the legs 28 of the anchor 14 in their stowed positions for illustrative purposes, the location of the legs 28 outside the sheath 18 immediately leads to the deployed configuration shown in FIG. 10. As with the arms 26, deployment of the legs 28 results from the shape-memory property of the anchor material causing the tips 40 of the legs 28 to move radially outward and disengage the windows 52 of the connector 50, and then arcuately travel in the distal direction to engage and become embedded in the proximal surface of the septum 54. Importantly, because the arms 26 and legs 28 are not collinear when stowed, the tips 34 and 40 of the arms 26 and legs 28 do not directly oppose each other when deployed. Finally, disengagement of the leg tips 40 from the connector 50 uncouples the anchor 14 from the connector 50, as evident from FIG. 10, so that the sheath 18 and positioning catheter 16 can be withdrawn together to leave the sensor 12 implanted in the septum 54 with the anchor 14 as depicted in FIG. 11.

The delivery system 100 represented in FIG. 12 is illustrated in FIGS. 12 through 22 in a manner corresponding to FIGS. 1 through 11 for the deliver system 10 of FIG. 1. In FIGS. 12 through 22, consistent reference numbers are used to identify functionally similar structures, but with a numerical prefix (1) added where appropriate to distinguish the embodiment from the previous embodiment of the invention. Because of the commonality of the delivery systems 10 and 100, only differences between the embodiments will be discussed in any detail, and the detailed description of the delivery system 10 is otherwise incorporated by reference into the following discussion of the delivery system 100.

As evident from comparing FIGS. 1 through 5 to FIGS. 12 through 16, the construction of the delivery system 100 (FIG. 12), the stowed and deployed configurations of its anchor 114 (FIGS. 13 and 14, respectively), and the release actions of its arms 126 (FIG. 14) are similar to that for the delivery system 10 of FIGS. 1 through 11. The most notable differences between the delivery systems 10 and 100 involve their legs 28 and 128, including their configurations, the manner in which they connect to their respective connectors 50 and 150, and the manner in which the legs 28 and 128 deploy. With regard to the last item, whereas the legs 28 of the delivery system 10 deploy primarily by continuously traveling along a substantially arcuate route toward the distal end of the anchor 14, the legs 128 of the delivery system 100 shown in FIGS. 12 through 22 have a compound deployment action, in which the legs 128 initially spread radially (FIGS. 19 and 20) and then travel axially in the distal direction until the tips 140 of the legs 128 engage and become embedded in the septum 54 (FIG. 21).

Figure 13:
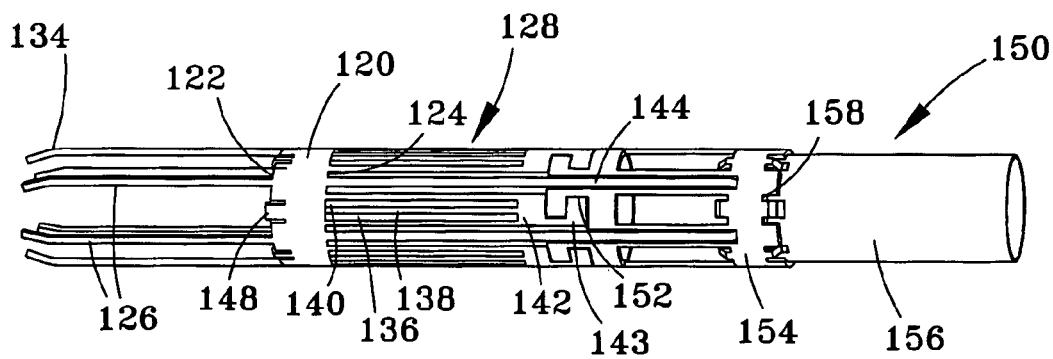
FIGS. 13 and 14 are isolated perspective views of an anchor of the implant delivery system of FIG. 12, showing the anchor in both stowed and deployed configurations, respectively.
Figure 14:
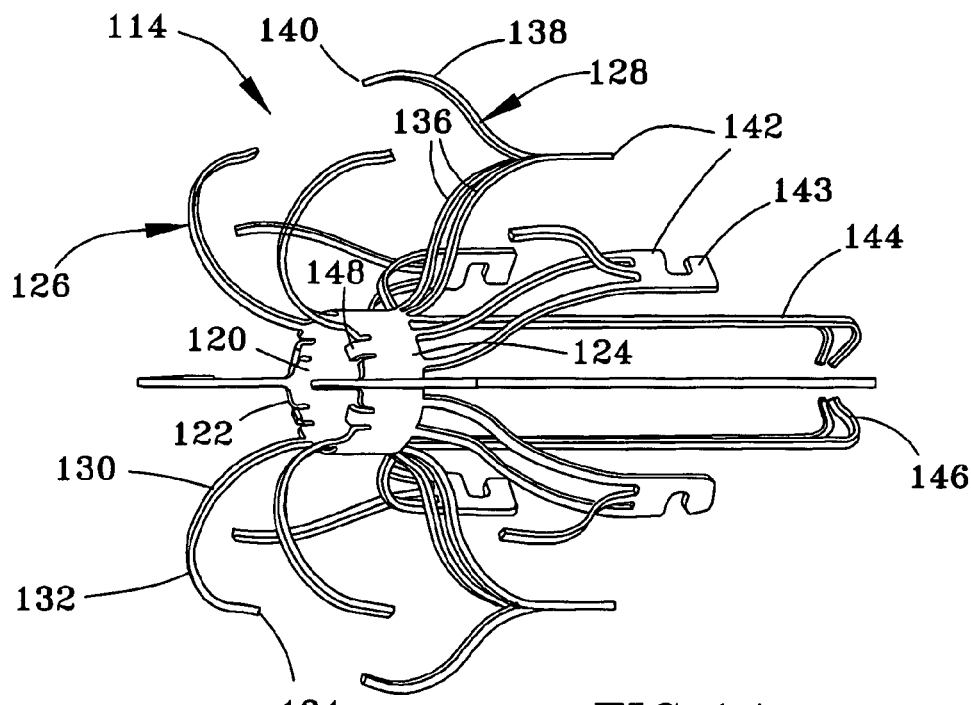

The embodiment of FIGS. 12 through 22 is represented as achieving the above by reconfiguring the legs 128 and connector 150 as shown in FIGS. 12 through 15. As evident from FIGS. 12, 13, and 14, the legs 128 are configured to have three primary sections: a first portion 136 that generally extends in the proximal direction from the proximal end 124 of the base 120, a tab 142 at the proximal end of each first portion 136, and a second portion 138 that extends from the tab 142 in the distal direction. Each first portion 136 is represented as being formed by two parallel bands spaced apart to define a slot 137 within which the corresponding second portion 138 is entirely received when the anchor 114 is in its stowed configuration (FIGS. 12 and 13). Each tab 142 defines a junction that interconnects its corresponding first and second portions 136 and 138. As evident in FIG. 14, the tab 142 serves as a base from which the first and second portions 136 and 138 extend and diverge to define a V-shaped cross-section in a plane coinciding with a radial of the base 120. Each second portion 138 terminates with an extremity or tip 140. All members 136, 137, 138, 140, and 142 of the legs 128 are generally parallel to but radially offset from the axis of the base 120. As with the previous embodiment, the arms 126 and the second portions 138 of the legs 128 are not collinear when stowed.

Each tab 142 defines a circumferentially-extending flange 143 sized and shaped to be received in a slot 152 on the connector 150, so that axial movement of the anchor 114 relative to the connector 150 is prevented when the anchor 114 is in its stowed configuration (FIGS. 12 and 13). By using the sheath 18 to hold the flanges 143 of the legs 128 in their respective slots 152, as is the case when the positioning catheter 16 and anchor 114 are disposed within the sheath 18

(FIG. 16), the anchor 114 is secured to the catheter 16 through its connector 150, but can be quickly released by retracting the sheath 18 to expose the legs 128 and thereby release the flanges 142 from their windows 152.

Figure 15:
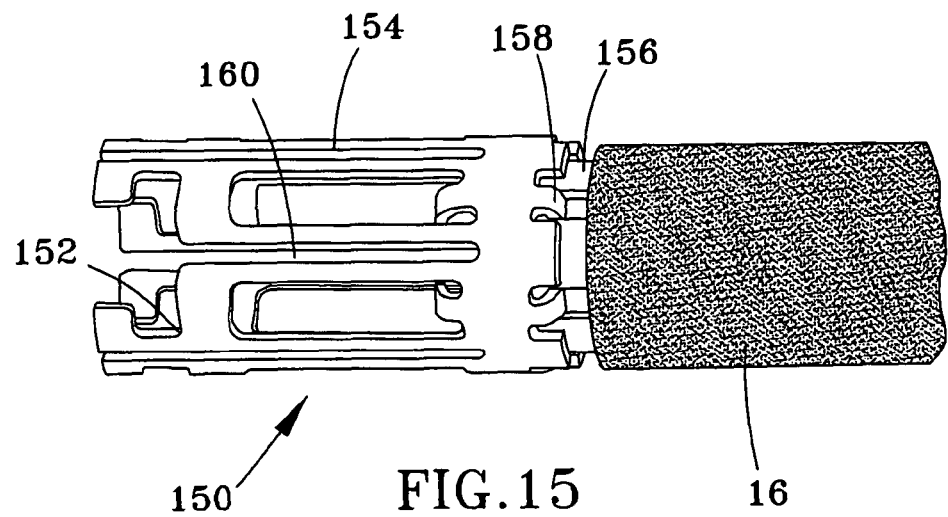
FIG. 15 is an isolated perspective view of a positioning catheter of the implant delivery system of FIG. 12.
Figure 16:
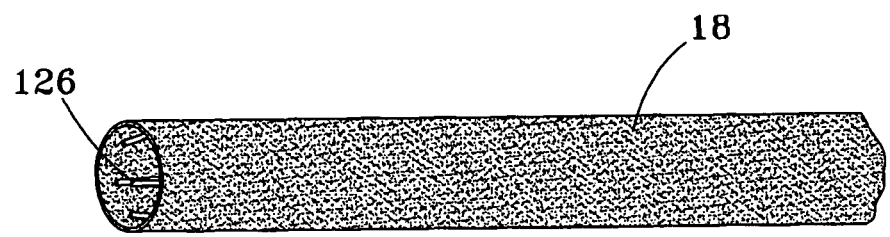
FIG. 16 is a perspective view of the implant delivery system of FIG. 12, showing the anchor and its implant retracted into a sheath in preparation for delivering the implant.

As evident from FIGS. 13 and 15, the connector 150 is an assembly that includes an articulating extension 154 coupled to a tubular base 156 by a number of fingers 158 (for example, by engaging the fingers 158 with windows in the base 156, corresponding to the windows 52 of the connector 50 in FIG. 4). As with the previous embodiment, this leg-connector coupling scheme does not form a rigid joint, but instead creates an articulating joint in that the extension 154 (and therefore the anchor 114 mounted to the extension 154) has some freedom of movement in directions transverse to the axis of the positioning catheter 16.

As with the first embodiment, the anchor 114 further includes retention legs 144 that extend from the proximal end 124 of the base 120 in the proximal direction and parallel to the axis of the base 120, with each retention leg 144 terminating with a finger 146 that extends radially inward toward the axis of the base 120. In combination with fingers 148 at the distal end 122 of the base 120, the base 120, retention legs 144, and fingers 146 define a cage for the implant 12, with opposite ends of the implant 12 abutting the fingers 146 and 148. Placement of the implant 12 within the cage can be achieved in the same manner as described for the first embodiment.

Figure 17:
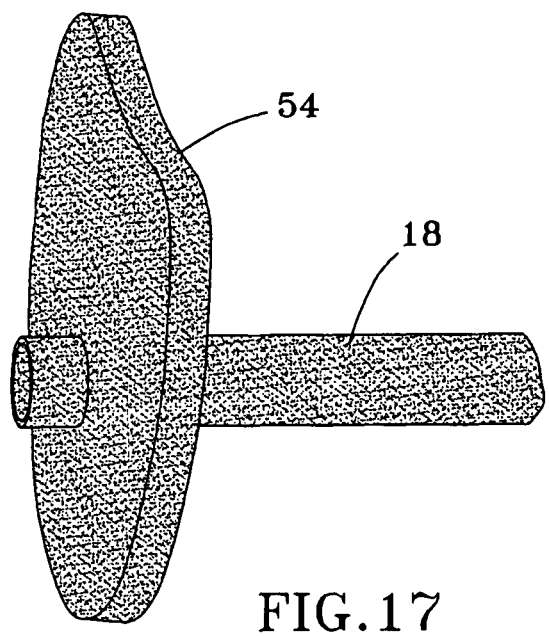
FIGS. 17 through 22 are perspective views representing procedural steps when placing the anchor and implant of FIG. 12.
Figure 18:
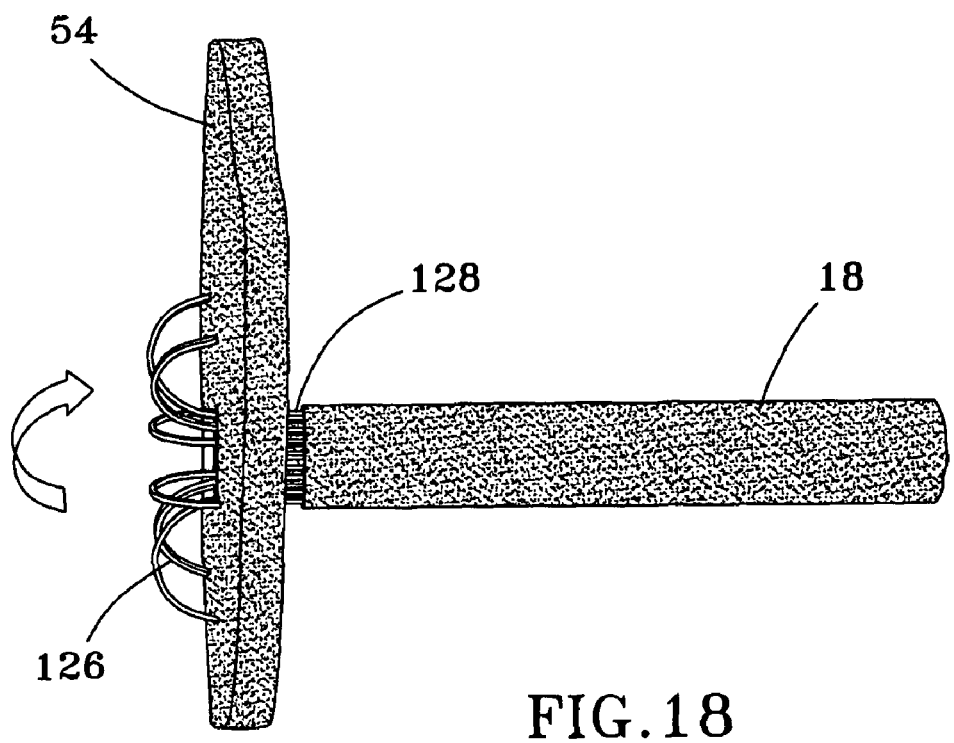
Figure 19:
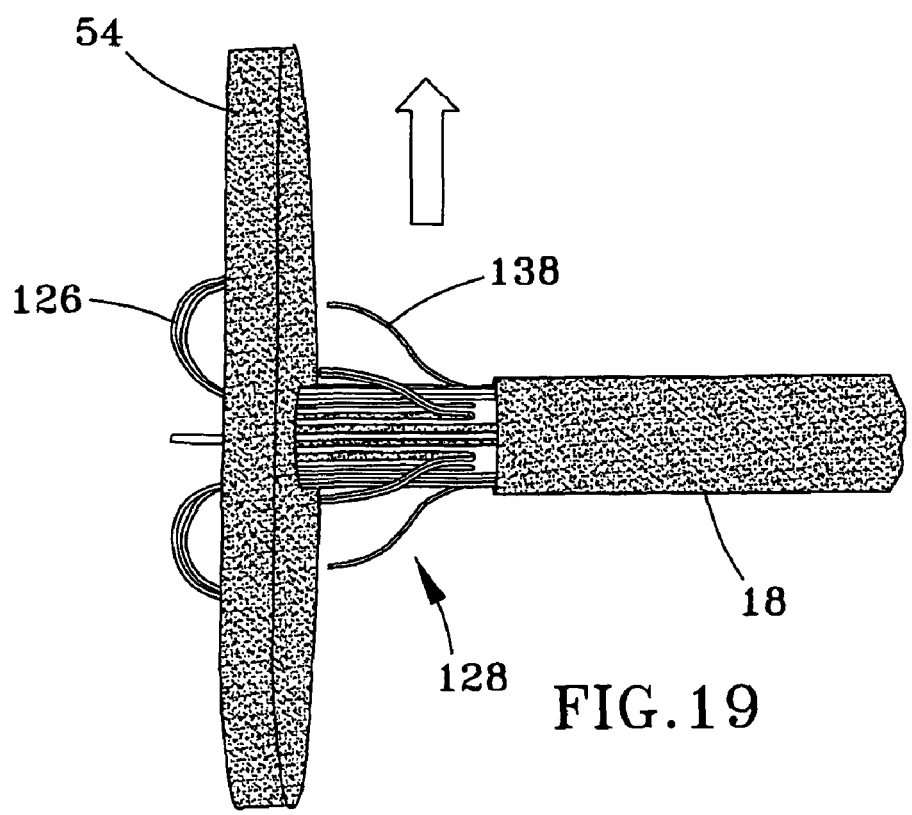
Figure 20:
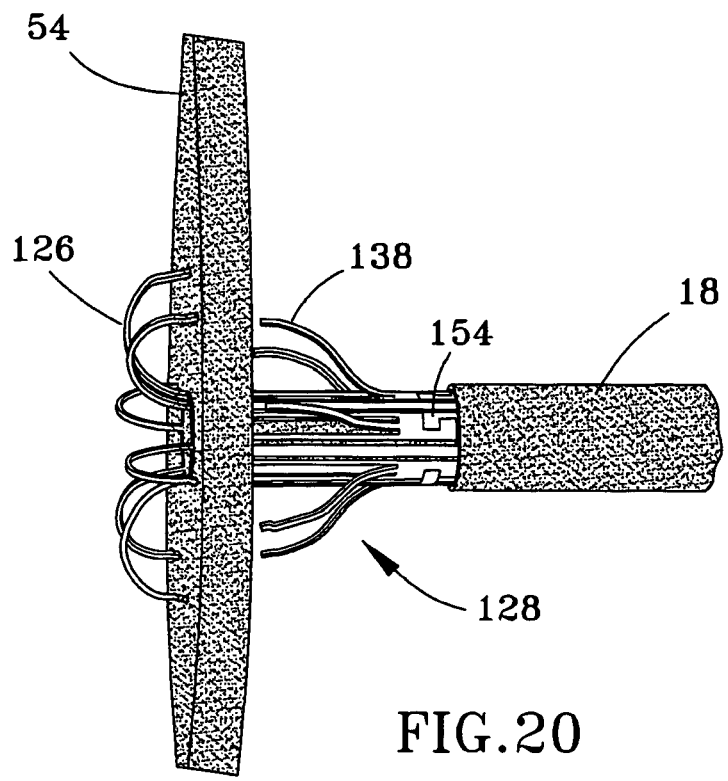
Figure 21:
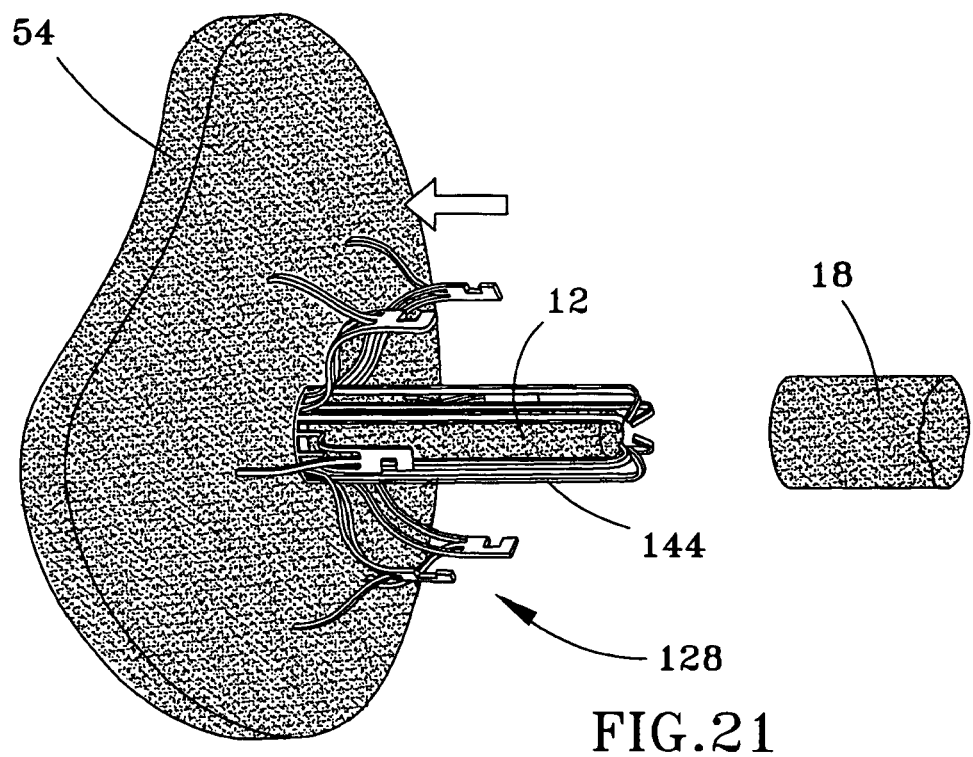
Figure 22:
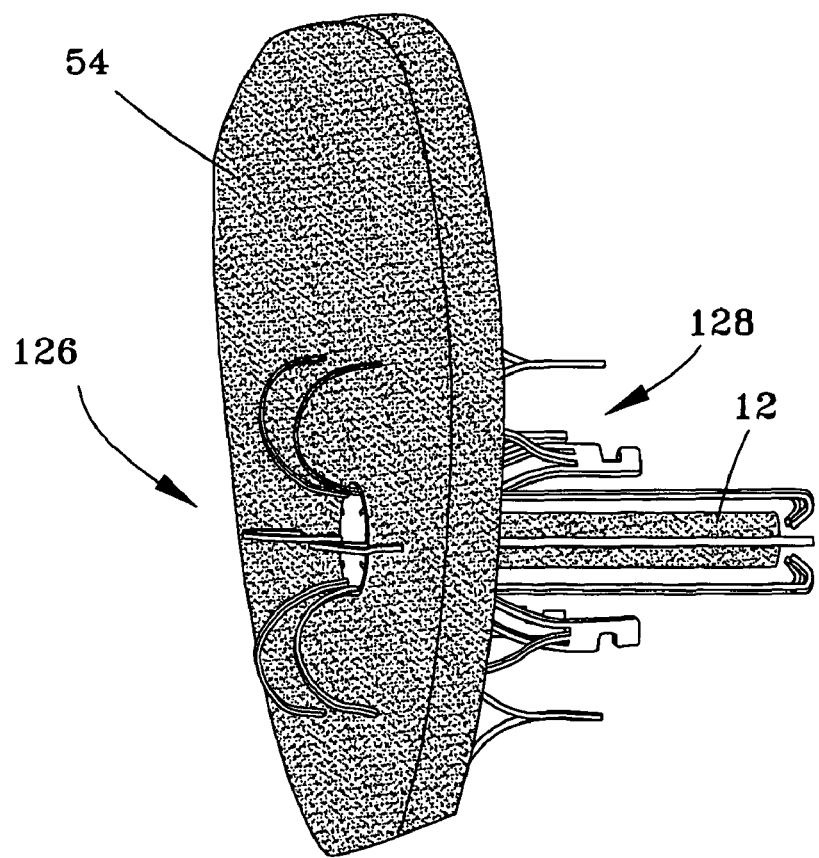

FIGS. 17 through 22 represent a series of steps depicting the procedure for delivering and implanting the anchor 114 and implant 12 in the atrial septum 54 (or other suitable wall). The procedure is similar to that described for the first embodiment, with the sequence of FIGS. 17 through 22 generally corresponding in sequence to that of FIGS. 6 through 11, respectively. As such, after the sheath 18 is passed through a patient's arterial system and placed through the atrial septum 54, the catheter 16 with its anchor 114 and implant 112 are passed through the sheath 18 until located within the distal end of the sheath 18 as shown in FIG. 17. FIG. 18 depicts the sheath 18 as having been sufficiently retracted to deploy the arms 126, resulting in the tips 134 of the arms 126 engaging and becoming embedded in the distal surface of the septum 54. The sheath 18 is then further retracted as sequentially depicted in FIGS. 19 and 20, with the former showing only the second portions 138 of the legs 128 being deployed as a result of moving radially outward. FIG. 20 shows the sheath 18 as sufficiently retracted to expose the entire lengths of the legs 128, though with the legs 128 remaining in their stowed positions for illustrative purposes. The transition between FIGS. 20 and 21 evidence that the sheath 18 has released the first portion 136 and tab 142 of each leg 128, resulting in their radially outward movement to decouple the flanges 143 from their corresponding slots 152 in the connector 150. In addition, FIG. 21 shows the legs 128 as having traveled in the distal direction, causing the tips 140 of the legs 128 to engage and become embedded in the proximal surface of the septum 54. Importantly, because the arms 126 and legs 128 are not collinear when stowed, the tips 134 and 140 of the arms 126 and legs 128 do not directly oppose each other when deployed. Finally, disengagement of the leg flanges 143 from the connector 150 uncouples the anchor 114 from the connector 150, as evident from FIG. 21, so that the sheath 18 and positioning catheter 16 can be withdrawn together to leave the sensor 12 implanted in the septum 54 with the anchor 114 as depicted in FIG. 22.

Figure 23:
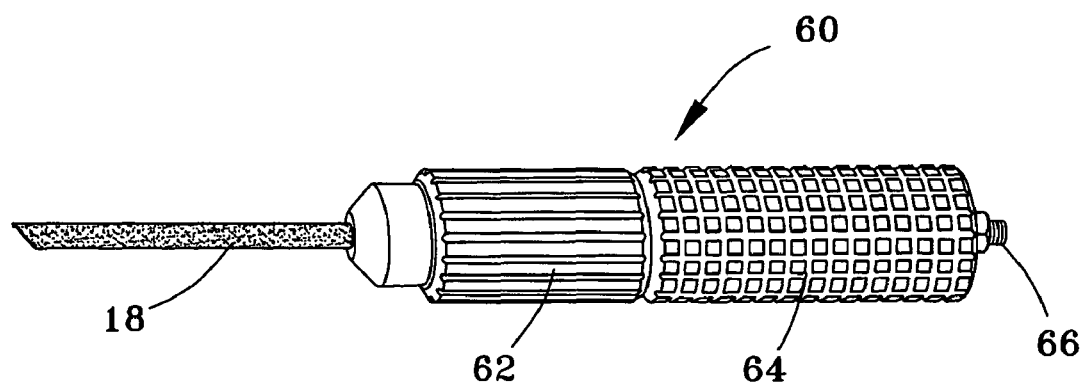
FIG. 23 is a perspective view representing a manipulator for use with the implant delivery systems of FIGS. 1 through 22.

FIG. 23 represents a manipulator 60 for use with the implant delivery systems 10 and 100 of FIGS. 1 through 22. The manipulator 60 functions to lock the positioning catheter 16 and sheath 18 together to precisely maintain their axial alignment. A rotational actuator ring 62 is coupled to the sheath 18 and provides precise control of the relatively small axial movements performed by the sheath 18, which in turn controls the deployment of the arms 26 and 126 and legs 28 and 128 of the anchors 14 and 114. The actuator ring 62 preferably operates with detents that provide tactile feel feedback to the operator, such that the operator is better informed of the relative positions of the catheter 16 and sheath 18 without visually checking. The handle 64 of the manipulator 60 enables the operator to have positive rotational control of the entire delivery system 10 or 100, such that the manipulator 60 has both rotational and axial control of the anchors 14 and 114 while threading the delivery systems 10 and 100 through a patient's arterial system. Finally, the manipulator 60 further includes a fluid port 66 at the end of the handle 64 to enable fluid insertion and withdrawal through the hollow positioning catheter 16.

In view of the manner in which the anchors 14 and 114 are coupled to their connectors 50 and 150 as described above, the operator has the option to retry placing the anchors 14 and 114 and their implants 12 any number of times before deploying the arms 26 and 126 and legs 28 and 128 and final detachment of the anchors 14 and 114 from their catheter 16 by retracting the sheath 18. The preferred use of a single catheter 16 and single sheath 18 is believed to be uncomplicated and readily within the skills of the ordinary cardiologist.

In addition to the delivery and anchoring of wireless implanted medical devices, the anchors 14 and 114 and delivery methods of this invention can be utilized for non-wireless applications. For example, a pressure sensor (or any other type of sensor) located in the left atrium (or elsewhere) can be provided with a communication connection to other medical devices (such as, but not limited to, pacemakers) from the right atrium side of the anchor/implant. Potential communication connections include, but are not limited to, electrical wires, pacemaker leads, flexible cables, optical connectors, ultrasonic pads, and electrophysiology signals. Hermetic electrical connection pads (instead of or in addition to a pressure sensor) can be provided from inside the implant 12 to its exterior. Such pads can be used to provide electrical connections to other medical devices, e.g., pacemakers, or provide electrical connections to other sensors (e.g., blood chemical sensors), which are made independently of implant 12 and anchors 14 and 114. Preferred locations for these pads are believed to be either of the flat ends of the cylindrical implant 12 shown in the Figures, for locating the pads in the left side, right side, or both sides of the heart.

While the invention has been described in terms of preferred embodiments, it is apparent that other forms could be adopted by one skilled in the art. Therefore, the scope of the invention is to be limited only by the following claims.

The invention claimed is:

1. An anchor for a medical implant, the anchor having a deployed configuration wherein the anchor comprises:
    a base member having an axis and first and second ends in oppositely-disposed first and second directions, respectively, along the axis of the base member;
    a plurality of arms radially projecting from the first end of the base member, each arm having a first portion extending in the first direction from the first end of the base member and a second portion extending in the second direction from the first portion thereof; and
    a plurality of legs radially projecting from the second end of the base member, each leg having a first portion extending in the second direction from the second end of the base member and a second portion extending in the first direction from the first portion thereof;

means for securing the medical implant to the base member so that at least a portion of the implant is between the first and second ends of the base member; and means for connecting the anchor to a connector;

wherein the arms and legs terminate at extremities that are opposing but not aligned with each other.

2. The anchor according to claim 1, wherein the base member has an annular shape.

3. The anchor according to claim 2, wherein the securing means comprises fingers extending radially inward from the annular shape of the base member toward the axis of the base member.

4. The anchor according to claim 1, wherein the securing means comprises appendages extending from the base member in the second direction.

5. The anchor according to claim 4, wherein the appendages are contiguous with and extend from the second end of the base member so as to be parallel to but spaced radially outward from the axis of the base member, each of the appendages terminating with a retention feature that extends radially inward toward the axis of the base member.

6. The anchor according to claim 5, wherein the securing means comprises a cage defined by the base member, the appendages, and the retention features thereof.

7. The anchor according to claim 1, wherein the connecting means comprises portions of the legs.

8. The anchor according to claim 1, wherein each of the arms is arcuate along its entire length.

9. The anchor according to claim 1, wherein the extremities of the arms are substantially parallel to but radially offset from the axis of the base member.

10. The anchor according to claim 1, wherein the extremities of the legs are substantially parallel to but radially offset from the axis of the base member.

11. The anchor according to claim 1, wherein each of the arms and legs entirely lies in a separate plane containing the axis of the base member.

12. The anchor according to claim 1, wherein the extremity of each arm and each leg defines a piercing tip.

13. The anchor according to claim 1, wherein the base member, the arms, the legs, and the connecting means are a unitary structure without metallurgical or mechanical joints therebetween.

14. The anchor according to claim 1, wherein the base member, and the connecting means are formed of a "shape memory" nickel-titanium alloy.

15. The anchor according to claim 1, wherein the arms and the legs are sufficiently pliable to enable being elastically deformed to acquire a stowed configuration of the anchor in which the arms extend parallel to the axis of the base member from the first end thereof and the legs extend parallel to the axis of the base member from the second end thereof.

16. The anchor according to claim 1, wherein each of the legs is arcuate along its entire length.

17. The anchor according to claim 16, wherein the extremities of the legs are substantially parallel to but radially offset from the axis of the base member.

18. The anchor according to claim 16, wherein each of the legs has a third portion between its second portion and its extremity, the third portions of the legs being oriented substantially radially relative to the axis of the base member.

19. The anchor according to claim 1, wherein the first and second portions of each leg are arcuate along their respective entire lengths, each of the legs further comprising a junction that interconnects the first and second portions thereof, each junction having a base from which the first and second portions thereof extend and diverge to define a V-shaped cross-section in a plane coinciding with a radial of the base member of the anchor.

20. The anchor according to claim 19, wherein the extremities of the legs are substantially parallel to but radially offset from the axis of the base member.

21. The anchor according to claim 19, wherein the junction of each leg further comprises a connector opposite the first and second portions thereof and extending from the base thereof in the second direction.

22. The anchor according to claim 19, wherein the first portion of each leg comprises at least two bands and a slot therebetween, and the second portion of each leg is sized to be received in the slot.

23. A method of manufacturing the anchor according to claim 1, the method comprising the steps of:

cutting a unitary tubular body to form a tubular-shaped anchor preform comprising the base member and portions configured to define the arms, the legs, and the connecting means of the anchor; and then deforming the portions of the tubular-shaped anchor preform to form the arms, the legs, and the connecting means of the anchor.

24. A delivery system for a medical implant, the delivery system comprising:

a catheter assembly comprising a catheter;

an anchor comprising a base member having first and second ends in oppositely-disposed first and second directions, arms and legs extending from the first and second ends, respectively, of the base member, and means for securing the medical implant to the base member; and means for connecting the anchor to the catheter, the connecting means comprising a joint that enables articulating movement of the anchor relative to the catheter in directions transverse to an axis of the catheter.

25. The delivery system according to claim 24, wherein the connecting means comprises extremities of the legs.

26. The delivery system according to claim 24, wherein the connecting means comprises:

a connector at one end of the catheter;

openings in the connector; and extremities of the legs engaged with the openings in the connector, wherein the joint is defined by the extremities of the legs in the openings in the connector.

27. The delivery system according to claim 24, wherein the connecting means comprises:

a connector at one end of the catheter;

an articulating member coupled to the connector so as to define the joint; and extremities of the legs engaged with the articulating member.

28. The delivery system according to claim 24, wherein the catheter is a hollow conduit.

29. The delivery system according to claim 24, further comprising a sheath in which the catheter is telescopically received.

30. The delivery system according to claim 29, wherein the anchor is stowed within the sheath and the arms and the legs of the anchor are sufficiently pliable to enable being elastically deformed to acquire a stowed configuration of the anchor in which the arms extend parallel to an axis of the base member from the first end thereof and the legs extend parallel to the axis of the base member from the second end thereof.

31. The delivery system according to claim 30, wherein the connecting means of the anchor comprises portions of the legs.

32. The delivery system according to claim 30, wherein the connecting means comprises:
    a connector at one end of the catheter;
    openings in the connector; and
    extremities of the legs releasably held in engagement with the openings in the connector by the sheath, wherein the joint is defined by the extremities of the legs in the openings of the connector.

33. The delivery system according to claim 30, wherein the connecting means comprises:
    a connector at one end of the catheter;
    an articulating member coupled to the connector so as to define the joint; and
    extremities of the legs releasably held in engagement with the articulating member by the sheath.

34. The delivery system according to claim 29, wherein the anchor is deployed outside the sheath to define a deployed configuration in which:
    the arms radially project from the first end of the base member, each arm having a first portion extending in the first direction from the first end of the base member and a second portion extending in the second direction from the first portion thereof; and
    the legs radially project from the second end of the base member, each leg having a first portion extending in the second direction from the second end of the base member and a second portion extending in the first direction from the first portion thereof;
    wherein the arms and legs terminate at extremities that are opposing but not aligned with each other.

35. The delivery system according to claim 34, wherein the base member has an annular shape.

36. The delivery system according to claim 35, wherein the securing means of the anchor comprises fingers extending radially inward from the annular shape of the base member toward the axis of the base member.

37. The delivery system according to claim 34, wherein the securing means comprises appendages extending from the base member in the second direction.

38. The delivery system according to claim 37, wherein the appendages are contiguous with and extend from the second end of the base member so as to be parallel to but spaced radially outward from the axis of the base member, each of the appendages terminating with a retention feature that extends radially inward toward the axis of the base member.

39. The delivery system according to claim 38, wherein the securing means comprises a cage defined by the base member, the appendages, and the retention features thereof.

40. A method of delivering a medical implant, the method comprising the steps of:
    coupling an anchor to an end of a catheter and securing the medical implant to the anchor, the anchor having an axis that is coaxial with the catheter;
    passing the catheter with the anchor coupled thereto through a sheath;
    placing an end of the sheath through an internal wall of a human body by moving the sheath in a first direction;
    with the anchor positioned within the sheath within the internal wall, moving the sheath in a second direction opposite the first direction to release a plurality of arms from the anchor that engage a distal surface of the internal wall; and
    further moving the sheath in the second direction to release a plurality of legs from the anchor that engage a proximal surface of the internal wall.

41. The method according to claim 40, wherein the anchor is coupled to the catheter by the legs of the anchor, and the anchor is decoupled from the catheter as a result of the legs being released by the sheath.

42. The method according to claim 40, wherein the anchor is coupled to the catheter so as to enable articulating movement of the anchor relative to the catheter in directions transverse to an axis of the catheter.

43. The method according to claim 40, wherein as the catheter is passed through the sheath, the anchor is in a stowed configuration in which the arms and the legs of the anchor are elastically deformed, the arms extend parallel to the axis of the anchor in the first direction and the legs extend parallel to the axis of the anchor in the second direction.

44. The method according to claim 43, wherein while in the stowed configuration the anchor is coupled to the catheter by the legs of the anchor, and the anchor is decoupled from the catheter as a result of the legs being released by the sheath.

45. The method according to claim 43, wherein as the sheath releases the arms, the arms radially expand so that each arm has a first portion extending in the first direction and a second portion extending in the second direction from the first portion thereof.

46. The method according to claim 43, wherein as the sheath releases the legs, the legs radially expand so that each leg has a first portion extending in the second direction and a second portion extending in the first direction from the first portion thereof.

47. The method according to claim 40, wherein as the sheath releases the legs, an extremity of each leg travels in the first direction from a stowed position remote from the internal wall to a deployed position in which the extremity engages the proximal surface of the internal wall.

48. The method according to claim 47, wherein the anchor is coupled to the catheter by the extremities of the legs, and the anchor is decoupled from the catheter as a result of the legs being released by the sheath.

49. The method according to claim 40, wherein as the sheath releases the legs, a first portion of each leg initially expands radially so that an extremity of the leg extends in the first direction, and thereafter a second portion of each leg subsequently expands radially so that the extremity of the leg travels in the first direction to engage the proximal surface of the internal wall.

50. The method according to claim 49, wherein the anchor is coupled to the catheter by third portions of the legs between the respective first and second portions thereof, and the anchor is decoupled from the catheter as a result of the legs being released by the sheath.

51. The method according to claim 40, wherein as a result of releasing the arms and the legs, extremities of the arms and the legs engage the distal and proximal surfaces of the internal wall, respectively, and the extremities of the arms are not aligned with the extremities of the legs.

52. The method according to claim 40, wherein as a result of releasing the arms and the legs, extremities of the arms and the legs pierce the distal and proximal surfaces of the internal wall, respectively, but do not pass through the internal wall.

53. The method according to claim 40, wherein the medical implant is a cardiovascular implant and the internal wall is a portion of a cardiovascular organ.

54. The method according to claim 53, wherein the internal wall is a septum of a heart.

55. The method according to claim 53, wherein the delivery of the medical implant is used in a procedure performed to diagnose, monitor, and/or treat a cardiovascular disease.

56. The method according to claim 40, wherein placement of the medical implant is used in a procedure performed to diagnose, monitor, and/or treat an internal organ.

* * * * *